United States Patent
Tang (10) Patent No.: US 11,589,818 B2
(45) Date of Patent: Feb. 28, 2023

(54) HEART RATE DETECTION METHOD AND WEARABLE DEVICE

(71) Applicant: GOERTEK INC., Shandong (CN)

(72) Inventor: Xianwei Tang, Weifang (CN)

(73) Assignee: GOERTEK INC., Weifang (CN)

( * ) Notice: Subject to any disclaimer, the term of this patent is extended or adjusted under 35 U.S.C. 154(b) by 413 days.

(21) Appl. No.: 16/764,354

(22) PCT Filed: Jul. 18, 2018

(86) PCT No.: PCT/CN2018/096188
§ 371 (c)(1),
(2) Date: May 14, 2020

(87) PCT Pub. No.: WO2019/100737
PCT Pub. Date: May 31, 2019

(65) Prior Publication Data
US 2020/0275891 A1  Sep. 3, 2020

(30) Foreign Application Priority Data

Nov. 23, 2017 (CN) .......................... 201711182778.9

(51) Int. Cl.
*A61B 5/00* (2006.01)
*G16H 40/60* (2018.01)
(Continued)

(52) U.S. Cl.
CPC ........ *A61B 5/6844* (2013.01); *A61B 5/02416* (2013.01); *A61B 5/02438* (2013.01);
(Continued)

(58) Field of Classification Search
CPC .............. A61B 5/6844; A61B 5/02416; A61B 5/02438; G01B 7/023; G16H 40/60
See application file for complete search history.

(56) References Cited

U.S. PATENT DOCUMENTS 9,782,128 B2  10/2017  Baek et al.
2014/0275852 A1*  9/2014  Hong ............... A61B 5/6844
                                              600/479
(Continued)

FOREIGN PATENT DOCUMENTS

CN   106484041 A   3/2017
CN   107981852 A   5/2018
(Continued)

OTHER PUBLICATIONS

Chinese Office Action dated Mar. 9, 2019 as received in Application No. 201711182778.9.
(Continued)

*Primary Examiner* — Joseph M Dietrich
(74) *Attorney, Agent, or Firm* — Maschoff Brennan (57) ABSTRACT

Provided are a heart rate detection method and a wearable device. The wearable device includes a casing, a processor installed in the casing, and an optical heart rate sensing module and a distance sensing module connected to the processor and installed on a side of the casing facing a wearing part of a user. The method includes: detecting, by the distance sensing module, a positional relationship between the optical heart rate sensing module and the wearing part of the user to obtain relative position data of the optical heart rate sensing module relative to the wearing part of the user; and adjusting a signal transmission power of the optical heart rate sensing module according to the relative position data, and detecting, by the optical heart rate sensing module, a heart rate of the user.

16 Claims, 3 Drawing Sheets

(51) Int. Cl.
    *A61B 5/024*     (2006.01)
    *G01B 7/02*     (2006.01)
    *G01L 5/00*     (2006.01)

(52) U.S. Cl.
    CPC .............. *A61B 5/681* (2013.01); *G01B 7/023* (2013.01); *G01L 5/00* (2013.01); *G16H 40/60* (2018.01); *A61B 2562/0247* (2013.01)

(56) References Cited

U.S. PATENT DOCUMENTS

| | | |
|---|---|---|
| 2016/0066790 A1 | 3/2016 | Lantsov et al. |
| 2016/0199002 A1 | 7/2016 | Baek et al. |
| 2017/0060178 A1 | 3/2017 | Ito |
| 2017/0296124 A1 | 10/2017 | Creemers et al. |
| 2018/0000418 A1 | 1/2018 | Li et al. |

FOREIGN PATENT DOCUMENTS

| | | |
|---|---|---|
| WO | 2016109918 A1 | 7/2016 |
| WO | 2016111592 A1 | 7/2016 |
| WO | 2017182456 A1 | 10/2017 |

OTHER PUBLICATIONS

Chinese Office Action dated Nov. 25, 2019 as received in Application No. 201711182778.9.

\* cited by examiner

HEART RATE DETECTION METHOD AND WEARABLE DEVICE

TECHNICAL FIELD

The present disclosure relates to the field of electronic technology, and in particular to a heart rate detection method and a wearable device.

BACKGROUND

With the rapid development of electronic technology, a wearable device may realize more and more functions by detecting the heart rate of a user, for example, exercise monitoring, health monitoring, sleep monitoring, etc.

In the prior art, the wearable device usually uses PPG (Photoplethysmography) pulse wave method to perform the heart rate detection. The PPG is a method for heart rate measurement based on the principle of photoelectric detection blood volume changes with pulse pulsation. The wearable device emits an optical signal to a wearing part of the user through an optical heart rate sensing module including an LED lamp and a photodetector and detects the reflection intensity of the optical signal. The heart rate of the user can be obtained by processing a change frequency of the obtained reflection intensity.

However, in the above heart rate detection method, when the user wears the wearable device, a relative position of the device and the wearing part of the user may change due to factors such as wearing too loose or movement, causing a change in the propagation path of the optical signal emitted by the optical heart rate sensing module, such that the reflection intensity of the optical signal detected by the optical heart rate sensing module becomes smaller, thereby the detection result of the heart rate is affected and the detection accuracy of the heart rate is reduced.

SUMMARY

In view of so, the present disclosure provides a heart rate detection method and a wearable device to solve the technical problem of the decreased detection accuracy of the heart rate caused by a change of a relative position of the wearable device and a wearing part, and further improves detection accuracy of the heart rate of the device.

In order to solve the above technical problem, the present disclosure provides a heart rate detection method, which is applied to a wearable device, where the wearable device includes a casing, a processor installed in the casing, and an optical heart rate sensing module and a distance sensing module connected to the processor and installed on a side of the casing facing a wearing part of a user;

the method includes:

detecting, by the distance sensing module, a positional relationship between the optical heart rate sensing module and the wearing part of the user to obtain relative position data of the optical heart rate sensing module relative to the wearing part of the user; and adjusting a signal transmission power of the optical heart rate sensing module according to the relative position data, and detecting, by the optical heart rate sensing module, a heart rate of the user.

The present disclosure further provides a wearable device, including a casing, a processor installed in the casing, and an optical heart rate sensing module and a distance sensing module connected to the processor and installed on a side of the casing facing a wearing part of a user; where the optical heart rate sensing module is used for emitting an optical signal and detecting a reflection intensity of the optical signal; and sending the reflection intensity to the processor;

the distance sensing module is used for sending a positional relationship between the optical heart rate sensing module and a wearing part of the user to the processor; and the processor is used for detecting the positional relationship between the optical heart rate sensing module and the wearing part of the user according to the distance sensing module, to obtain relative position data of the optical heart rate sensing module relative to the wearing part of the user; and adjusting a signal transmission power of the optical heart rate sensing module according to the relative position data, and detecting the heart rate of the user through the optical heart rate sensing module.

Compared with the prior art, the present disclosure may obtain the following technical effect:

The present disclosure provides a heart rate detection method and a wearable device. The wearable device includes a casing, a processor installed in the casing, and an optical heart rate sensing module and a distance sensing module connected to the processor and installed on a side of the casing facing a wearing part of a user. The method detects a positional relationship between the optical heart rate sensing module and the wearing part of the user through the distance sensing module, and calculates and obtains relative position data of the optical heart rate sensing module relative to the wearing part of the user according to the detected positional relationship. The change of the optical path of the optical signal emitted by the optical heart rate sensing module may be acquired through the relative position data, so that the signal transmission power of the optical heart rate sensing module may be dynamically adjusted according to the relative position data to compensate the attenuation of the reflected optical intensity caused by the change of the optical path. The problem of inaccurate result of the heart rate detection due to the change of the relative position of the optical heart rate sensing module relative to the wearing part is avoided, and the detection accuracy of the heart rate is greatly improved.

DETAILED DESCRIPTION OF EXAMPLE EMBODIMENTS

The embodiments of the present disclosure will be described in detail below in conjunction with the accompanying drawings and examples, so as to fully understand and implement the implementation process of how the present disclosure uses technical means to solve technical problems and achieve technical effects.

In order to solve the technical problem of decreased detection accuracy of the heart rate caused by the change of the relative position of the smart wearable device and the wearing part, the present disclosure provides a heart rate detection method and a wearable device. The wearable device includes a casing, a processor installed in the casing, and an optical heart rate sensing module and a distance sensing module connected to the processor and installed on a side of the casing facing a wearing part of a user. The method detects a positional relationship between the optical heart rate sensing module and the wearing part of the user through the distance sensing module, and calculates and obtains relative position data of the optical heart rate sensing module relative to the wearing part of the user according to the detected positional relationship. The change of the optical path of the optical signal emitted by the optical heart rate sensing module may be acquired through the relative position data, so that the signal transmission power of the optical heart rate sensing module may be dynamically adjusted according to the relative position data to compensate the attenuation of the reflected optical intensity caused by the change of the optical path. The problem of inaccurate result of the heart rate detection due to the change of the relative position of the optical heart rate sensing module relative to the wearing part is avoided, and the detection accuracy of the heart rate is greatly improved.

The technical solution of the present disclosure will be described in detail below with reference to the drawings.

Figure 1:
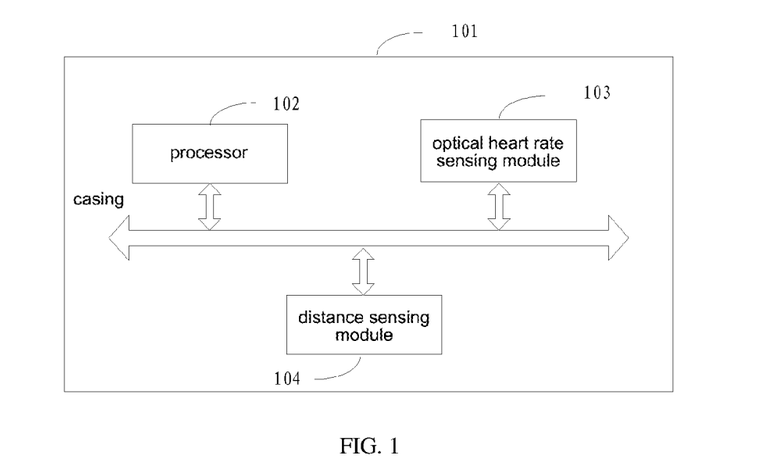
FIG. 1 is a functional block diagram of an embodiment of a wearable device according to an embodiment of the present disclosure.

FIG. 1 is a functional block diagram of an embodiment of a wearable device according to an embodiment of the present disclosure. The wearable device may include a casing 101, a processor 102 installed in the casing 101, and an optical heart rate sensing module 103 and a distance sensing module 104 which are connected to the processor 102 and installed on a side of the casing 101 facing a wearing part of a user.

The optical heart rate sensing module 103 is used for emitting an optical signal and detecting a reflection intensity of the optical signal; and sending the reflection intensity to the processor 102.

In the embodiment of the present disclosure, the heart rate is detected based on the PPG (PhotoPlethysmoGraphy) pulse wave method. Therefore, the detection of the heart rate of the user is achieved by installing the optical heart rate sensing module 103. However, this heart rate detection method is extremely susceptible to the use environment, especially the wearing style, such as the tightness of the wear and the fit degree with the wearing part of the user, which directly affects the propagation and measurement of the optical signal. When the user wears the heart rate detection device to perform exercise, the influence of the position change between the optical heart rate sensing module and the wearing part of the user on the measurement result due to the movement is particularly significant.

The optical heart rate sensing module 103 may include plurality sets of LED (short for light emitting diode) lights for emitting the optical signal, and one or more photodetectors for detecting of the optical intensity of the optical signal reflected by the wearing part of the user. When the optical heart rate sensing module 103 is attached with the wearing part of the user, a plurality of optical signals emitted by the plurality sets of LED lights enter the wearing part of the user perpendicularly, and are reflected by the wearing part of the user to generate a reflected optical signal. One or more photodetectors detect the optical intensity of the plurality of the reflected optical signals. Because the reflection value of the human skin, bones, muscles, fat, etc. to light is a fixed value, and the reflection value of the capillary and the arterial venous blood vessels to the optical signal always changes with the change of the pulse volume, where its change regular pattern is consistent with the heart rate, the heart rate of the user can be detected and obtained through detecting the change of the reflection intensity of the optical signal by the optical heart rate sensing module 103.

The distance sensing module 104 is used for sending the detected positional relationship between the optical heart rate sensing module 103 and the wearing part of the user to the processor 102.

The processor 102 is used for detecting the positional relationship between the optical heart rate sensing module 103 and the wearing part of the user according to the distance sensing module 104, and obtaining relative position data of the optical heart rate sensing module 103 relative to the wearing part of the user; and adjusting the signal transmission power of the optical heart rate sensing module 103 according to the relative position data, and detecting the heart rate of the user through the optical heart rate sensing module 103.

Because the optical heart rate sensing module 103 obtains the heart rate of the user by detecting the change rule of the reflection intensity of the optical signal, when the positional relationship between the optical heart rate sensing module 103 and the wearing part of the user changes, the optical path of the optical signal emitted by the optical heart rate sensing module 103 is not perpendicular to the wearing part of the user but an incident angle is generated, which leads to the reflection intensity of the optical signal detected by the photodetector will become smaller, thereby affecting the accuracy of heart rate detection. Therefore, by detecting the positional relationship between the optical heart rate sensing module 103 and the wearing part of the user by the distance sensing module 104, calculating and obtaining the relative position data of the optical heart rate sensing module 103 and the wearing part of the user according to the positional relationship by the processor 102, and dynamically adjusting the signal strength of the optical signal emitted by the optical heart rate sensing module 103 according to the position data, the attenuation of the reflection intensity of the optical signal caused by the change in the optical path is compensated.

The distance sensing module 104 may detect the positional relationship between the optical heart rate sensing module 103 and the wearing part of the user in real time or within a preset interval, so that the processor 102 may calculate and obtain the relative position data of the optical heart rate sensing module 103 relative to the wearing part of the user based on the positional relationship in time.

In the embodiment of the present disclosure, by detecting the positional relationship between the optical heart rate sensing module and the wearing part of the user by the distance sensing module in real time, and calculating and obtaining the relative position data by the processor according to the positional relationship to dynamically adjust the optical intensity of the optical signal emitted by the optical heart rate sensing module, the accuracy of the heart rate of the user detected by the optical heart rate sensing module is ensured, and the detection accuracy of the heart rate is greatly improved.

In order to more accurately detect the positional relationship between the optical heart rate sensing module 103 and the wearing part of the user, the distance sensing module 104 may include a plurality of capacitive sensors. The optical heart rate sensing module 103 is installed at a central position on the side of the casing 101 facing the wearing part of the user, and the plurality of capacitive sensors surround a periphery of the optical heart rate sensing module at equal intervals by taking the optical heart rate sensing module 103 as a center.

The processor 102 may further be used for: for each capacitive sensor, calculating a user distance between a position point on the casing 101 corresponding to the capacitive sensor and the wearing part of the user based on a capacitance parameter detected by the capacitive sensor; and calculating and obtaining the relative position data of the optical heart rate sensing module 103 and the wearing part of the user based on a plurality of user distances.

The plurality of capacitive sensors may be used for detecting the capacitance parameters of the casing 101 at different positions relative to the wearing part of the user. For each capacitive sensor, a user distance between a position point on the casing 101 corresponding to the capacitive sensor and the wearing part of the user may be calculated based on a capacitance parameter detected by the capacitive sensor.

It should be noted that the processor 102 calculating and obtaining the user distance from each capacitive sensor to the wearing part of the user for each capacitance parameter may include: for each capacitance parameter, calculating and obtaining the user distance from each capacitive sensor to the wearing part of the user in accordance with the calculation formula of the user distance as below.

The calculation formula of the user distance may be expressed as: $H=\varepsilon*S/C$;

H represents the user distance from any one capacitive sensor to the wearing part of the user, C represents the capacitance parameter detected by any one capacitive sensor, $\varepsilon$ represents the air dielectric constant, and S represents the surface area of any one capacitive sensor.

Since each capacitive sensor is disposed on the surface of the casing 101, and the plurality of the capacitive sensors surround the periphery of the optical heart rate sensing module at equal intervals by taking the optical heart rate sensing module as a center, the calculated and obtained positional relationship of the casing 101 relative to the wearing part of the user may be approximated to the positional relationship of the optical heart rate sensing module 103 relative to the wearing part of the user.

In the embodiment of the present disclosure, by disposing the plurality of capacitive sensors on the side of the casing facing the wearing part of the user, calculating and obtaining the user distance from the wearing part of the user to each capacitive sensor through the capacitance parameter detected by the capacitive sensor, the positional relationship of the casing relative to the wearing part of the user may be known from a plurality of orientations, the relative position data of the optical heart rate sensing module at the center of the casing relative to the wearing part of the user is for further calculated and obtained.

In order to accurately reflect the change of the relative position of the wearable device and the wearing part of the user during the movement of the user, the change of the relative position may generally be reflected according to two parameters of distance and inclination. Therefore, the relative position data of the optical heart rate sensing module 103 relative to the wearing part of the user may include a relative offset distance and a relative offset angle. Optionally, the calculating and obtaining the relative position data of the optical heart rate sensing module 103 and the wearing part of the user based on a plurality of user distances may include:

calculating an average user distance from the plurality of the capacitive sensors to the wearing part of the user based on the plurality of the user distances;

determining the average user distance as a relative offset distance between the optical heart rate sensing module 103 and the wearing part;

determining a third capacitive sensor and a fourth capacitive sensor with a largest user distance difference and central symmetric about the optical heart rate sensing module 103 based on the plurality of the user distances; and calculating and obtaining the relative offset angle between the optical heart rate sensing module 103 and the wearing part of the user based on a third user distance detected by the third capacitive sensor, a fourth user distance detected by the fourth capacitive sensor, and a third interval distance between the third capacitive sensor and the fourth capacitive sensor (a straight-line distance).

It should be noted that, calculating the average user distance from the plurality of capacitive sensors to the wearing part of the user based on the plurality of the user distances may be calculated and obtained in accordance with the calculation formula as below:

$$H_{ave} = \sum_{i=1}^{N} H_i/N.$$

The relative offset distance is determined as: $h=H_{ave}$.

Since the plurality of the capacitive sensors surround the periphery of the optical heart rate sensing module at equal intervals by taking the optical heart rate sensing module 103 as the center, every two capacitive sensors in the plurality of the capacitive sensors are central symmetric about the optical heart rate sensing module. During the movement of the user, the wearable device shifts to cause the casing 101 to not fit the wearing part of the user. At this time, there will be an angle between the casing 101 and the wearing part of the user. By comparing every two user distance differences that are central symmetric about the optical heart rate sensing module 103, it may be determined that the connection line of the two capacitive sensors with the largest user distance difference is located in the direction of the casing offset from the wearing part of the user.

Actually, in the engineering production stage of the wearable device, the interval distance between every two capacitive sensors central symmetric about the optical heart rate sensing module 103 is measured in advance and is stored in the processor 102 in advance. After the two capacitive sensors with the largest user distance difference are determined, the interval distance (straight line distance) between the two capacitive sensors may be obtained, and then the relative offset angle of the optical heart rate sensing module and the wearing part of the user may be calculated and obtained according to the calculation formula of the triangle angle.

Therefore, the relative offset angle of the optical heart rate sensing module 103 and the wearing part of the user may be calculated and obtained in accordance with the calculation formula of the relative offset angle as below, based on the third user distance detected by the third capacitive sensor, the fourth user distance detected by the fourth capacitive sensor, and the third interval distance between the third capacitive sensor and the fourth capacitive sensor;

The calculation formula of the relative offset angle is: $\alpha=\arcsin[(Hd-Hg)/Ddg]$;

Hd represents the third user distance, Hg represents the fourth user distance, and Ddg represents the third interval distance.

The embodiment of the present disclosure is not only applicable to the calculation of the relative offset data when the casing of the wearable device is attached and fitted to the wearing part of the user, but also applicable when the casing of the wearable device is completely detached (there is no attachment part). It is therefore more suitable for scenarios where the power of the optical signal emitted by the optical heart rate sensing module of the wearable device is dynamically adjusted when the user has a large motion range.

After obtaining the relative position data of the optical heart rate sensing module 103 and the wearing part of the user, it is necessary to obtain the attenuation data of the reflection intensity of the optical signal according to the correspondence between the reflection intensity of the optical signal and the relative position data. Therefore, the intensity value of the optical signal emitted by the optical heart rate sensing module is correspondingly enhanced according to the attenuation data of the reflection intensity, to compensate the reflection intensity of the optical signal measured by the optical heart rate sensing module.

It should be noted that the adjusting the signal transmission power of the optical heart rate sensing module 103 according to the relative position data, and detecting the heart rate of the user through the optical heart rate sensing module 103 may include:

determining an attenuation coefficient corresponding to the relative offset distance according to a preset attenuation parameter adjustment rule;

where, the preset attenuation parameter adjustment rule is stored in the wearable device in advance, and the preset attenuation parameter adjustment rule comprises a corresponding relationship between the relative offset distance and the attenuation coefficient;

calculating attenuation multiple of the reflection intensity based on the attenuation coefficient and the relative offset angle; and adjusting the signal transmission power of the optical heart rate sensing module 103 in accordance with the attenuation multiple, and detecting the heart rate of the user through the optical heart rate sensing module 103.

Actually, in the engineering production stage of the wearable device, in the standard test environment, the different relative offset angles and relative offset distances of the optical heart rate sensing module 103 provided on the surface of the casing 101 and the wearing part of the user are measured to obtain the attenuation data of the corresponding optical signal, and the attenuation coefficient model of the optical signal is establish according to the test result. By storing the attenuation coefficient model in the processor 102 in advance, after calculating and obtaining the relative offset distance and the relative offset angle of the current optical heart rate sensing module 103 relative to the wearing part of the user, the corresponding attenuation coefficient k(h) may be inquired according to the attenuation coefficient model.

It should be noted that when the intensity of the optical signal emitted by the optical heart rate sensing module 103 is R, after the relative position changes, the reflection intensity of the signal light detected by the optical heart rate sensing module 103 is:

$$R(h,\alpha)=k(h)*\cos^2(\alpha)*R.$$

In practical applications, the calculating the attenuation multiple of the reflection intensity based on the attenuation coefficient and the relative offset angle may include:

calculating and obtaining the attenuation multiple of the reflection intensity based on the attenuation coefficient and relative offset angle, in accordance with the calculation formula of the attenuation multiple as below;

the attenuation multiple of the calculation formula is: $M=k(h)*\cos^2(\alpha)$;

M represents the attenuation multiple, h represents the relative offset distance, and k(h) represents the attenuation coefficient corresponding to the relative offset distance h.

Therefore, after the optical heart rate sensing module 103 detects that the reflection intensity of the obtained optical signal is weakened, the signal transmission power of the optical heart rate sensing module may be adjusted to 1/M of the original according to the calculated and obtained attenuation multiple of the reflection intensity to maintain the stability of the receipt signal of the optical heart rate sensing module 103.

In the embodiment of the present disclosure, by establishing the attenuation coefficient model of the attenuation coefficient of the optical signal with the relative offset angle and the relative offset distance based on the pre-test, the attenuation coefficient correspond to the optical signal may be inquired through the calculated and obtained relative offset angle and relative offset distance. The attenuation multiple of the reflection intensity may be calculated according to the attenuation coefficient, so that the processor may dynamically adjust the transmission power of the optical heart rate sensing module in real time according to the calculated attenuation multiple, the stability of the receipt optical signal of the optical heart rate sensing module is ensured, the reflection intensity obtained by the detection is not disturbed by factors such as the outside world and changes in the optical path, and the accuracy of heart rate detection is greatly improved.

Figure 2:
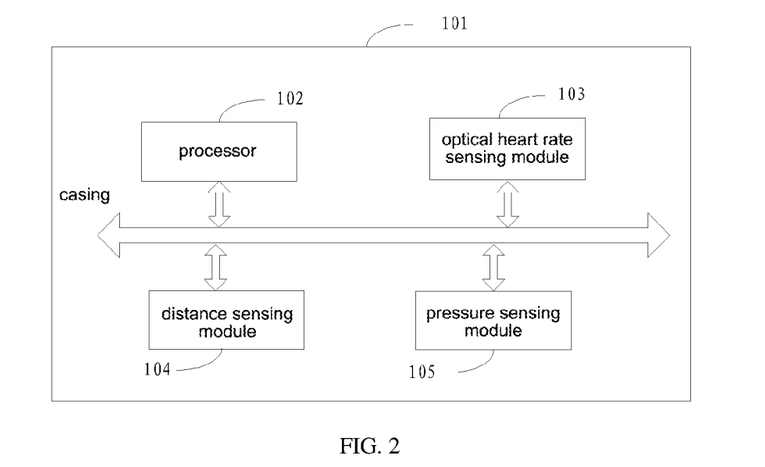
FIG. 2 is a functional block diagram of another embodiment of a wearable device according to an embodiment of the present disclosure.

FIG. 2 is a schematic block diagram of another embodiment of a wearable device according to an embodiment of the present disclosure. The wearable device includes a casing 101 in the embodiment of FIG. 1, a processor 102 installed in the casing 101, and in addition to the optical heart rate sensing module 103 and the distance sensing module 104 connected to the processor 102 and installed on the side of the casing 101 facing the wearing part of the user, a pressure sensing module 105 connected to the processor 102 and installed on the side of the casing 101 facing the wearing part of the user is also included.

The pressure sensing module 105 may include a plurality of pressure sensors, and the plurality of pressure sensors surround a periphery of the optical heart rate sensing module 103 at equal intervals by taking the optical heart rate sensing module 103 as a center, and are disposed at intervals with respect to the plurality of capacitive sensors.

The pressure sensing module 105 is used for detecting and sending a pressure parameter between the casing 101 and the wearing part of the user to the processor 102. Specifically, for each pressure sensor in the pressure sensing module 105, the pressure sensor is used for detecting the pressure value between the position point corresponding to the pressure sensor on the casing 101 and the wearing part of the user, and generating the pressure parameter corresponding to the pressure sensor.

The processor 102 calculating and obtaining the relative position data of the optical heart rate sensing module 103 and the wearing part of the user based on a plurality of user distances may include:

determining a first pressure sensor and a second pressure sensor corresponding to a first largest and a second largest pressure parameters respectively based on each pressure parameter; determining a capacitive sensor located between the first pressure sensor and the second pressure sensor as a first capacitive sensor and a second capacitive sensor central symmetric to the first capacitive sensor about the optical heart rate sensing module 103; and calculating and obtaining the relative position data of the optical heart rate sensing module 103 relative to the wearing part of the user according to the user distances detected by the first capacitive sensor and the second capacitive sensor.

When the wearable device casing 101 is partially offset from the wearing part of the user and still partly attached to the wearing part of the user, a plurality of pressure sensors are provided to detect the pressure parameters at different positions on the casing, so that the processor may quickly determine the two capacitive sensors with the largest user distance difference based on the detected pressure parameters.

In the embodiment of the present disclosure, in order to further reduce the workload of the processor when there are more capacitive sensors, the plurality of the pressure sensors are disposed at a periphery of the optical heart rate sensing module 103 at equal intervals by taking the optical heart rate sensing module 103 as a center, and are disposed at intervals with respect to the plurality of capacitive sensors. The embodiment of the present disclosure obtains the first largest and second largest pressure values from the plurality of the pressure values detected by the plurality of the pressure sensors, and thus may directly determine the first capacitive sensor is closest to the user distance of the wearing part of the user, and the second capacitive sensor central symmetric to the first capacitive sensor is the capacitive sensor with the furthest user distance. Therefore, the first capacitive sensor and the second capacitive sensor with the largest user distance difference may be directly determined, and it is not necessary to calculate the user distance difference of every two central symmetric capacitive sensors one by one, which may greatly improve the processing efficiency of the processor.

It can be seen from the embodiment of FIG. 1 that the relative position data of the optical heart rate sensing module 103 relative to the wearing part of the user may include a relative offset distance and a relative offset angle. Therefore, the calculating and obtaining the relative position data of the optical heart rate sensing module 103 relative to the wearing part of the user according to the user distance detected by the first capacitive sensor and the second capacitive sensor, may include:

calculating and obtaining a relative offset distance of the optical heart rate sensing module 103 relative to the wearing part of the user according to a first user distance detected by the first capacitive sensor, a second user distance detected by the second capacitive sensor, a first interval distance between the first capacitive sensor and the second capacitive sensor, and a second interval distance between the first pressure sensor or the second pressure sensor and the optical heart rate sensing module; and calculating and obtaining a relative offset angle between the optical heart rate sensing module and the wearing part of the user based on the first user distance, the second user distance, and the first interval distance.

The interval distance between each pressure sensor and the optical heart rate sensing module 103 is measured and stored in advance in the wearable device engineering production stage. Since each pressure sensor is symmetrical about the center line, the interval distance between each pressure sensor and the optical heart rate sensing module 103 refers to the vertical distance from each pressure sensor to the center line.

It should be noted that the calculating and obtaining a relative offset distance of the optical heart rate sensing module 103 and the wearing part of the user according to a first user distance detected by the first capacitive sensor, a second user distance detected by the second capacitive sensor, a first interval distance between the first capacitive sensor and the second capacitive sensor, and a second interval distance between the first pressure sensor or the second pressure sensor and the optical heart rate sensing module 103 may include:

calculating and obtaining the relative offset distance between the optical heart rate sensing module 103 and the wearing part of the user based on the first user distance, the second user distance, the first interval distance, and the second interval distance, in accordance with a calculation formula of the relative offset distance as below:

the calculation formula of the relative offset distance is: $h=(Ha-He)*Dcd/Dae$;

h represents the relative offset distance, Ha represents the first user distance, He represents the second user distance, Dae represents the first interval distance, and Dcd represents the second interval distance.

Based on the principle of parallel line segmentation proportionality, the first user distance, the second user distance and the relative offset distance are all parallel lines perpendicular to the wearing part of the user, and the first interval distance is parallel to the second interval distance. According to the principle of parallel line segmentation proportionality, the ratio of the first interval distance to the second interval distance is equal to the ratio of the user distance difference between the first capacitive sensor and the second capacitive sensor to the relative offset distance, so that the relative offset distance is calculated and obtained.

The calculating and obtaining a relative offset angle between the optical heart rate sensing module 103 and the wearing part of the user based on the first user distance, the second user distance, and the first interval distance may include:

calculating and obtaining the relative offset angle between the optical heart rate sensing module 103 and the wearing part of the user based on the first user distance, the second user distance, and the first interval distance, in accordance with a calculation formula of the relative offset angle as below;

the calculation formula of the relative offset angle is: $\alpha=\arcsin[(Ha-He)/Dae]$.

The calculation method of the relative offset angle is the same as the calculation method in the embodiment of FIG. 1, and details are not described herein again.

In the embodiment of the present disclosure, the first capacitive sensor and the second capacitive sensor with the largest user distance difference are determined by the pressure parameters detected by the provided plurality of the pressure sensors, and the relative offset distance is obtained based on the principle of parallel line segmentation proportionality, so that the value of the relative offset distance obtained by calculating the average user distance is more accurate, calculation error caused by averaging is avoided, the calculation accuracy of the relative offset distance and the relative offset angle are improved. Thereby the calculated and obtained attenuation multiple of the reflection intensity is more accurate, and the accuracy of the heart rate measurement of the optical heart rate sensing module is further improved.

In a practical application, the optical heart rate sensing module 103 may include one photodetector and two sets of LED lights, the two sets of LED lights are respectively connected to the processor 102 to realize the dynamic adjustment of the transmission power of the optical heart rate sensing module signal 103. The photodetector is located in the center of the optical heart rate sensing module 103, and two sets of LED lights are symmetrically arranged on the left and right sides of the photodetector, so that the photodetector may detect the reflection intensity of the obtained optical signal.

In an actual application, the wearable device may further include a fixing belt connected to the casing 101, and the fixing belt is used for fixing the wearable device to the wearing part of the user.

Generally, the two ends of the casing 101 of the wearable device are used to connect the fixing belt. During the movement of the user, the position shift of the casing is usually the casing on one side of the fixing belt tilting up, and the other side attaches and fits with the wearing part of the user. In order to accurately detect the positional relationship of the casing 101 relative to the wearing part of the user, the distance sensing module 104 may include four capacitive sensors; the four capacitive sensors surround a periphery of the optical heart rate sensing module 103 at equal intervals by taking the optical heart rate sensing module 103 as a center; and where two capacitive sensors of the four capacitive sensors are disposed at the two ends of the casing 101 connected to the fixing belt respectively.

The pressure sensing module 105 may further include four pressure sensors; the four pressure sensors and the four capacitance sensors are disposed at equal intervals, and surround a periphery of the optical heart rate sensing module 103 at equal intervals.

Figure 3:
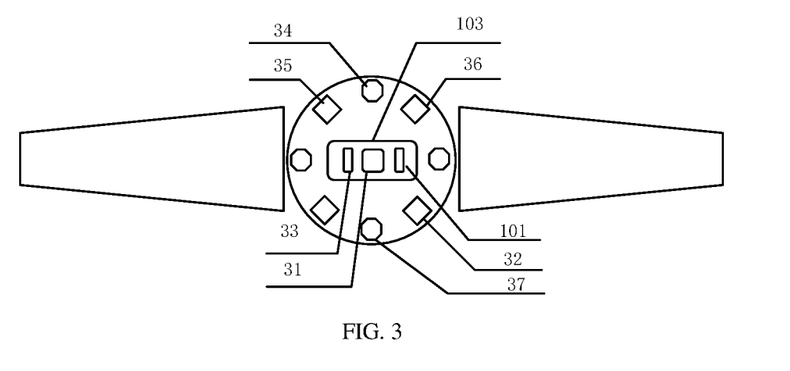
FIG. 3 is a schematic diagram of the back structure of a wearable device according to an embodiment of the present disclosure.

The wearable device may be a smart bracelet or a smart watch. FIG. 3 shows a back view of any smart watch. The optical heart rate sensing module 103 is located in the center of the casing 101, and the optical heart rate sensing module 103 includes one photodetector 31 and two sets of LED lights 32 and 33. The distance sensing module 104 and the pressure sensing module 105 surround a periphery of the optical heart rate sensing module 103 at equal intervals by taking the optical heart rate sensing module 103 as a center. The distance sensing module 104 includes 4 capacitive sensors (the octagon shown in FIG. 3 represents the capacitive sensor), and the pressure sensing module includes 4 pressure sensors (the diamond shown in FIG. 3 represents the pressure sensor). The processor 102 is located in the casing 101 and is connected to the distance sensing module 104 and the pressure sensing module 105 by the optical heart rate sensing module 103 respectively, which is not shown in FIG. 3.

Figure 4:
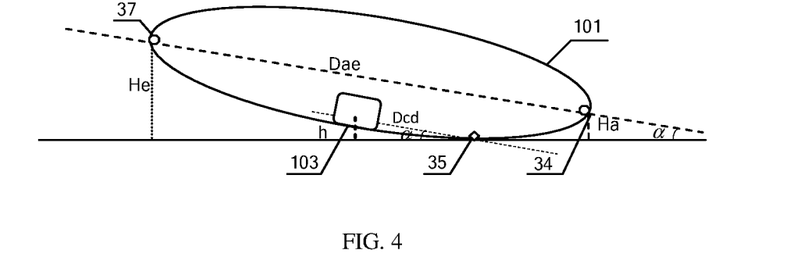
FIG. 4 is a schematic side view when a relative position of a wearable device and a wearing part changes according to an embodiment of the present disclosure.

In this smart watch, the back of the watch case is attached to the wearing part of the user through the strap to perform heart rate detection through the optical heart rate sensing module 103. During the movement of the user, the position shift and the inclination angle are happened on the smart watch case 101 with respect to the wearing part of the user, as shown in FIG. 4 which shows a schematic side view when a relative position of a wearable device and a wearing part changes. At this time, the pressure sensor 35 is attached to the wearing part of the user. At this time, the pressure parameter value detected by the pressure sensor 35 and the pressure sensor 36 are the largest, so that the capacitance sensor 34 between the pressure sensor 35 and the pressure sensor 36 may be determined as the first capacitance sensor, and the capacitive sensor 37 central symmetric to the capacitive sensor 34 about the optical heart rate sensing module 103 is the second capacitive sensor. Dae is the interval distance between the capacitive sensor 34 and the capacitive sensor 37, that is, the first interval distance (straight line distance); Dcd is the interval distance between the optical heart rate sensing module 103 and the pressure sensor 35 or the pressure sensor 36 (where, the pressure sensor 35 or the pressure sensor 36 are symmetrical about the center line, and the interval distance is the vertical distance of the pressure sensor 35 or the pressure sensor 36 from the center line), that is, the second interval distance; Ha is the first user distance, and He is the second user distance. Therefore, the relative offset distance h may be calculated through the above calculation formula of the relative offset distance, and the relative offset angle α may be calculated according to the above calculation formula of the relative offset angle.

Further, the corresponding attenuation coefficient is inquired according to the calculated and obtained relative offset distance h and relative offset angle α, and the attenuation multiple of the reflection intensity of the optical signal is calculated and obtained, so that the processor may adjust the signal transmission power of the optical heart rate sensing module in real time according to the attenuation multiple, and the accuracy of the heart rate detection of the device is improved greatly.

Figure 5:
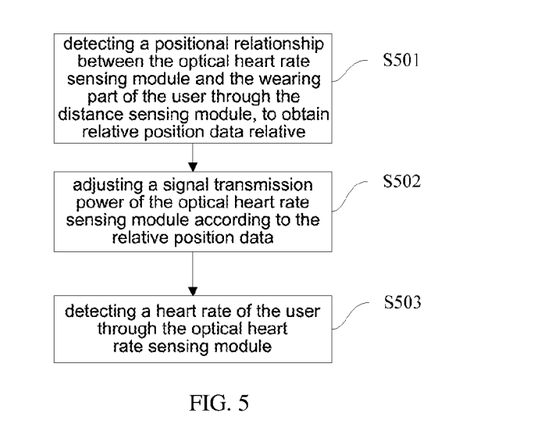
FIG. 5 is a flowchart of an embodiment of a heart rate detection method according to an embodiment of the present disclosure.

FIG. 5 is a flowchart of an embodiment of a heart rate detection method according to an embodiment of the present disclosure, which is applied to a wearable device. The wearable device includes a casing, a processor installed in the casing, and an optical heart rate sensing module and a distance sensing module connected to the processor and installed on a side of the casing facing a wearing part of a user.

The method may include:

S501: detecting a positional relationship between the optical heart rate sensing module and the wearing part of the user through the distance sensing module, to obtain relative position data of the optical heart rate sensing module relative to the wearing part of the user;

S502: adjusting a signal transmission power of the optical heart rate sensing module according to the relative position data; and S503: detecting a heart rate of the user through the optical heart rate sensing module.

The foregoing has described in detail the feasible solutions of the embodiments of the present disclosure, which will not be repeated here.

In the embodiment of the present disclosure, by detecting the positional relationship between the optical heart rate sensing module and the wearing part of the user by the distance sensing module in real time, and calculating and obtaining the relative position data by the processor according to the positional relationship to dynamically adjust the optical intensity of the optical signal emitted by the optical heart rate sensing module, the accuracy of the heart rate of the user detected by the optical heart rate sensing module is ensured, and the detection accuracy of the heart rate is greatly improved.

In order to more accurately detect the positional relationship between the optical heart rate sensing module and the wearing part of the user, the distance sensing module may include a plurality of capacitive sensors. The optical heart rate sensing module is installed at a central position on the side of the casing facing the wearing part of the user, and the plurality of capacitive sensors surround a periphery of the optical heart rate sensing module at equal intervals by taking the optical heart rate sensing module as a center.

The detecting a positional relationship between the optical heart rate sensing module and the wearing part of the user through the distance sensing module, to obtain relative position data of the optical heart rate sensing module relative to the wearing part of the user may include:

for each capacitive sensor, calculating a user distance between a position point on the casing corresponding to the capacitive sensor and the wearing part of the user based on a capacitance parameter detected by the capacitive sensor; and calculating and obtaining the relative position data of the optical heart rate sensing module and the wearing part of the user based on a plurality of user distances.

It should be noted that the processor calculating and obtaining the user distance from each capacitive sensor to the wearing part of the user for each capacitance parameter may include: for each capacitance parameter, calculating and obtaining the user distance from each capacitive sensor to the wearing part of the user in accordance with the calculation formula of the user distance as below.

The calculation formula of the user distance may be expressed as: $H=\varepsilon*S/C$;

H represents the user distance from any one capacitive sensor to the wearing part of the user, C represents the capacitance parameter detected by any one capacitive sensor, $\varepsilon$ represents the air dielectric constant, and S represents the surface area of any one capacitive sensor.

In the embodiment of the present disclosure, by disposing the plurality of capacitive sensors on the side of the casing facing the wearing part of the user, calculating and obtaining the user distance from the wearing part of the user to each capacitive sensor through the capacitance parameter detected by the capacitive sensor, the positional relationship of the casing relative to the wearing part of the user may be known from a plurality of orientations, the relative position data of the optical heart rate sensing module at the center of the casing relative to the wearing part of the user is for further calculated and obtained.

In order to accurately reflect the change of the relative position of the wearable device and the wearing part of the user during the movement of the user, the change of the relative position may generally be reflected according to two parameters of distance and inclination. Therefore, the relative position data of the optical heart rate sensing module relative to the wearing part of the user may include a relative offset distance and a relative offset angle. Optionally, the calculating and obtaining the relative position data of the optical heart rate sensing module and the wearing part of the user based on a plurality of user distances may include:

calculating an average user distance from the plurality of the capacitive sensors to the wearing part of the user based on the plurality of the user distances;

determining the average user distance as a relative offset distance between the optical heart rate sensing module and the wearing part;

determining a third capacitive sensor and a fourth capacitive sensor with a largest user distance difference and central symmetric about the optical heart rate sensing module based on the plurality of the user distances; and calculating and obtaining the relative offset angle between the optical heart rate sensing module and the wearing part of the user based on a third user distance detected by the third capacitive sensor, a fourth user distance detected by the fourth capacitive sensor, and a third interval distance between the third capacitive sensor and the fourth capacitive sensor.

It should be noted that, calculating the average user distance from the plurality of capacitive sensors to the wearing part of the user based on the plurality of the user distances may be calculated and obtained in accordance with the calculation formula as below:

$$H_{ave} = \sum_{i=1}^{N} H_i/N;$$

The relative offset distance is determined as: $h=H_{ave}$.

The relative offset angle of the optical heart rate sensing module and the wearing part of the user may be calculated and obtained in accordance with the calculation formula of the relative offset angle as below, based on the third user distance detected by the third capacitive sensor, the fourth user distance detected by the fourth capacitive sensor, and the third interval distance between the third capacitive sensor and the fourth capacitive sensor;

The calculation formula of the relative offset angle is: $\alpha=\arcsin[(Hd-Hg)/Ddg]$;

Hd represents the third user distance, Hg represents the fourth user distance, and Ddg represents the third interval distance.

The embodiment of the present disclosure is not only applicable to the calculation of the relative offset data when the casing of the wearable device is attached and fitted to the wearing part of the user, but also applicable when the casing of the wearable device is completely detached (there is no attachment part). It is therefore more suitable for scenarios where the power of the optical signal emitted by the optical heart rate sensing module of the wearable device is dynamically adjusted when the user has a large motion range.

It should be noted that the adjusting the signal transmission power of the optical heart rate sensing module according to the relative position data, and detecting the heart rate of the user through the optical heart rate sensing module may include: determining an attenuation coefficient corresponding to the relative offset distance according to a preset attenuation parameter adjustment rule;

Where, the preset attenuation parameter adjustment rule is stored in the wearable device in advance, and the preset attenuation parameter adjustment rule comprises a corresponding relationship between the relative offset distance and the attenuation coefficient;

calculating attenuation multiple of the reflection intensity based on the attenuation coefficient and the relative offset angle; and adjusting the signal transmission power of the optical heart rate sensing module in accordance with the attenuation multiple, and detecting the heart rate of the user through the optical heart rate sensing module.

In practical applications, the calculating the attenuation multiple of the reflection intensity based on the attenuation coefficient and the relative offset angle may include:

calculating and obtaining the attenuation multiple of the reflection intensity based on the attenuation coefficient and relative offset angle, in accordance with the calculation formula of the attenuation multiple as below;

the attenuation multiple of the calculation formula is: $M=k(h)*\cos^2(\alpha)$;

M represents the attenuation multiple, h represents the relative offset distance, and k(h) represents the attenuation coefficient corresponding to the relative offset distance h.

Therefore, after the optical heart rate sensing module detects that the reflection intensity of the obtained optical signal is weakened, the signal transmission power of the optical heart rate sensing module may be adjusted to 1/M of the original according to the calculated and obtained attenuation multiple of the reflection intensity to maintain the stability of the receipt signal of the optical heart rate sensing module.

In the embodiment of the present disclosure, by establishing the attenuation coefficient model of the attenuation coefficient of the optical signal with the relative offset angle and the relative offset distance based on the pre-test, the attenuation coefficient correspond to the optical signal may be inquired through the calculated and obtained relative offset angle and relative offset distance. The attenuation multiple of the reflection intensity may be calculated according to the attenuation coefficient, so that the processor may dynamically adjust the transmission power of the optical heart rate sensing module in real time according to the calculated attenuation multiple, the stability of the receipt optical signal of the optical heart rate sensing module is ensured, the reflection intensity obtained by the detection is not disturbed by factors such as the outside world and changes in the optical path, and the accuracy of heart rate detection is greatly improved.

Figure 6:
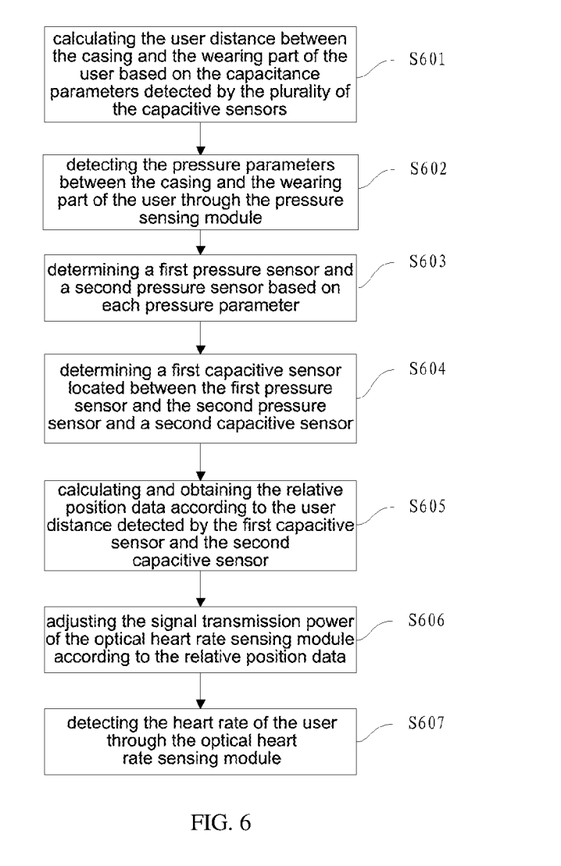
FIG. 6 is a flowchart of another embodiment of a heart rate detection method according to an embodiment of the present disclosure.

FIG. 6 is a flowchart of another embodiment of a heart rate detection method according to an embodiment of the present disclosure. The method may be applied to a wearable device.

The wearable device includes a casing in the embodiment of FIG. 5, a processor installed in the casing, and in addition to the optical heart rate sensing module and the distance sensing module connected to the processor and installed on the side of the casing facing the wearing part of the user, a pressure sensing module connected to the processor and installed on the side of the casing facing the wearing part of the user is also included.

The pressure sensing module may include a plurality of pressure sensors, and the plurality of pressure sensors surround a periphery of the optical heart rate sensing module at equal intervals by taking the optical heart rate sensing module as a center, and are disposed at intervals with respect to the plurality of capacitive sensors.

The method may include:

S601: calculating the user distance between the different positions on the casing detected by the plurality of the capacitive sensors and the wearing part of the user based on the capacitance parameters detected by the plurality of the capacitive sensors;

S602: detecting the pressure parameters between the different positions on the casing and the wearing part of the user through the pressure sensing module;

S603: determining a first pressure sensor and a second pressure sensor corresponding to the two pressure parameters with the largest and second largest values respectively based on each pressure parameter;

S604: determining that the capacitive sensor located between the first pressure sensor and the second pressure sensor is a first capacitive sensor, and a second capacitive sensor central symmetric to the first capacitive sensor about the optical heart rate sensing module;

S605: calculating and obtaining the relative position data of the optical heart rate sensing module relative to the wearing part of the user according to the user distance detected by the first capacitive sensor and the second capacitive sensor;

S606: adjusting the signal transmission power of the optical heart rate sensing module according to the relative position data; and S607: detecting the heart rate of the user through the optical heart rate sensing module.

The calculating and obtaining the relative position data of the optical heart rate sensing module relative to the wearing part of the user according to the user distance detected by the first capacitive sensor and the second capacitive sensor may include:

calculating and obtaining a relative offset distance of the optical heart rate sensing module relative to the wearing part of the user according to a first user distance detected by the first capacitive sensor, a second user distance detected by the second capacitive sensor, a first interval distance between the first capacitive sensor and the second capacitive sensor, and a second interval distance between the first pressure sensor or the second pressure sensor and the optical heart rate sensing module; and calculating and obtaining a relative offset angle between the optical heart rate sensing module and the wearing part of the user based on the first user distance, the second user distance, and the first interval distance.

It should be noted that the calculating and obtaining a relative offset distance of the optical heart rate sensing module and the wearing part of the user according to a first user distance detected by the first capacitive sensor, a second user distance detected by the second capacitive sensor, a first interval distance between the first capacitive sensor and the second capacitive sensor, and a second interval distance between the first pressure sensor or the second pressure sensor and the optical heart rate sensing module may include: calculating and obtaining the relative offset distance between the optical heart rate sensing module 103 and the wearing part of the user based on the first user distance, the second user distance, the first interval distance, and the second interval distance, in accordance with a calculation formula of the relative offset distance as below, and the calculation formula of the relative offset distance is: h=(Ha−He)*Dcd/Dae;

h represents the relative offset distance, Ha represents the first user distance, He represents the second user distance, Dae represents the first interval distance, and Dcd represents the second interval distance.

The calculating and obtaining a relative offset angle between the optical heart rate sensing module and the wearing part of the user based on the first user distance, the second user distance, and the first interval distance may include: calculating and obtaining the relative offset angle between the optical heart rate sensing module 103 and the wearing part of the user based on the first user distance, the second user distance, and the first interval distance, in accordance with a calculation formula of the relative offset angle as below;

the calculation formula of the relative offset angle is: α=arcsin [(Ha−He)/Dae].

The foregoing has described in detail the feasible solutions of the embodiments of the present disclosure, which will not be repeated here.

In the embodiment of the present disclosure, the first capacitive sensor and the second capacitive sensor with the largest user distance difference are determined by the pressure parameters detected by the provided plurality of the pressure sensors, and the relative offset distance is obtained based on the principle of parallel line segmentation proportionality, so that the value of the relative offset distance obtained by calculating the average user distance is more accurate, calculation error caused by averaging is avoided, the calculation accuracy of the relative offset distance and the relative offset angle are improved. Thereby the calculated and obtained attenuation multiple of the reflection intensity is more accurate, and the accuracy of the heart rate measurement of the optical heart rate sensing module is further improved.

In a typical configuration, a computing device includes one or more processors (CPUs), an input/output interface, a network interface, and a memory.

The memory may include a non-permanent memory, a random access memory (RAM), and/or a non-volatile memory in a computer-readable medium, such as a read-only memory (ROM) or a flash RAM. The memory is an example of a computer-readable medium.

The computer-readable medium includes permanent and non-permanent, mobile and non-mobile media, which may implement information storage by any method or technology. The information may be a computer-readable instruction, a data structure, a program module, or other data. Examples of computer storage media include, but are not limited to, a phase change RAM (PRAM), a static random access memory (SRAM), a dynamic random access memory (DRAM), other types of random access memories (RAMs), a read-only memory (ROM), an electrically erasable programmable read-only memory (EEPROM), a flash memory or other memory technologies, a compact disk read-only memory (CD-ROM), a digital versatile disk (DVD) or other optical memories, a magnetic tape cartridge, a magnetic tape storage device or other magnetic storage devices or any other non-transmission media, which may be used to store information accessible by a computing device. As defined herein, the computer-readable medium does not include non-transitory computer-readable media such as modulated data signals and carrier waves.

Certain words in the description and claims are used to refer to specific components. Those skilled in the art will understand that hardware manufacturers may use different terms to refer to the same component. This specification and claims do not use the differences in names as a way to distinguish components, but the differences in functions of components as a criterion for distinguishing between components. As used throughout the specification and claims, "comprising" is an open-ended term and should be interpreted as "including but not limited to". "approximately" means that within the acceptable error range, those skilled in the art can solve the technical problem within a certain error range, and basically achieve the technical effect. In addition, the term "coupling" includes any direct and indirect electrical coupling means. Therefore, if a first apparatus is described as being coupled to a second apparatus, it means that the first apparatus can be directly electrically coupled to the second apparatus, or indirectly electrically coupled to the second device through other apparatuses or coupling means. The subsequent description of the specification is a preferred embodiment for implementing the present disclosure, but the description is for the purpose of illustrating the general principles of the present disclosure and is not intended to limit the scope of the present disclosure. The scope of protection of the present disclosure shall be determined by the scope defined by the appended claims.

It is also to be noted that terms "include", "contain" or any other variants thereof are intended to include nonexclusive inclusions, thereby ensuring that a commodity or system including a series of elements not only includes those elements but also includes other elements which are not clearly listed or further includes elements intrinsic to the commodity or the system. Under the condition of no more restrictions, an element defined by statement "including a/an" does not exclude existence of another element which is the same in a commodity or system including the element.

The above description shows and describes several preferred embodiments of the present disclosure, but as mentioned before, it should be understood that the present disclosure is not limited to the form disclosed herein, and should not be regarded as an exclusion of other embodiments, but can be used for each other combinations, modifications, and environments, and can be altered within the scope of the application concept described herein, through the teachings above or related technology or knowledge in the relevant field. Modifications and changes made by those skilled in the art without departing from the spirit and scope of the present disclosure should all fall within the protection scope of the appended claims of the present disclosure.

What is claimed is:

1. A heart rate detection method, which is applied to a wearable device, wherein the wearable device comprises a casing, a processor installed in the casing, and an optical heart rate sensing module and a distance sensing module connected to the processor and installed on a side of the casing facing a wearing part of a user;

the method comprising:
   detecting, by the distance sensing module, a positional relationship between the optical heart rate sensing module and the wearing part of the user to obtain relative position data of the optical heart rate sensing module relative to the wearing part of the user; and
   adjusting a signal transmission power of the optical heart rate sensing module according to the relative position data, and detecting, by the optical heart rate sensing module, a heart rate of the user;
wherein the relative position data of the optical heart rate sensing module relative to the wearing part of the user comprises a relative offset distance and a relative offset angle;
the adjusting the signal transmission power of the optical heart rate sensing module according to the relative position data, and the detecting, by the optical heart rate sensing module, the heart rate of the user comprises:
   determining an attenuation coefficient corresponding to the relative offset distance according to a preset attenuation parameter adjustment rule; wherein, the preset attenuation parameter adjustment rule is stored in the wearable device in advance, and the preset attenuation parameter adjustment rule comprises a corresponding relationship between the relative offset distance and the attenuation coefficient;
   calculating attenuation multiple of a reflection intensity based on the attenuation coefficient and the relative offset angle; and
   adjusting the signal transmission power of the optical heart rate sensing module in accordance with the attenuation multiple, and detecting, by the optical heart rate sensing module, the heart rate of the user.

2. The method according to claim 1, wherein the distance sensing module comprises a plurality of capacitive sensors, the optical heart rate sensing module is installed at a central position on the side of the casing facing the wearing part of the user, and the plurality of capacitive sensors surround a periphery of the optical heart rate sensing module at equal intervals by taking the optical heart rate sensing module as a center;

the detecting, by the distance sensing module, the positional relationship between the optical heart rate sensing module and the wearing part of the user to obtain the relative position data of the optical heart rate sensing module relative to the wearing part of the user comprises:

for each capacitive sensor, calculating a user distance between a position point on the casing corresponding to the capacitive sensor and the wearing part of the user based on a capacitance parameter detected by the capacitive sensor; and calculating and obtaining the relative position data of the optical heart rate sensing module and the wearing part of the user based on a plurality of user distances.

3. The method according to claim 2, wherein the calculating and obtaining the relative position data of the optical heart rate sensing module and the wearing part of the user based on the plurality of user distances comprises:

selecting a first capacitive sensor closest to the wearing part of the user and a second capacitive sensor central symmetric to the first capacitive sensor about the optical heart rate sensing module; and calculating and obtaining the relative position data of the optical heart rate sensing module relative to the wearing part of the user according to the user distances detected by the first capacitive sensor and the second capacitive sensor.

4. The method according to claim 3, wherein the wearable device further comprises a pressure sensing module connected to the processor and disposed on the side of the casing facing the wearing part of the user; the pressure sensing module comprises a plurality of pressure sensors; and the plurality of pressure sensors surround a periphery of the optical heart rate sensing module at equal intervals by taking the optical heart rate sensing module as a center, and are disposed at intervals with respect to the plurality of capacitive sensors;

the method further comprising:

detecting, by the pressure sensing module, a pressure parameter between the casing and the wearing part of the user;

wherein the selecting the first capacitive sensor closest to the wearing part of the user comprises:

determining a first pressure sensor and a second pressure sensor corresponding to a first largest and a second largest pressure parameters respectively based on each pressure parameter; and determining a capacitive sensor located between the first pressure sensor and the second pressure sensor as the first capacitive sensor.

5. The method according to claim 4, wherein the calculating and obtaining the relative position data of the optical heart rate sensing module relative to the wearing part of the user according to the user distances detected by the first capacitive sensor and the second capacitive sensor comprises:

calculating and obtaining a relative offset distance between the optical heart rate sensing module and the wearing part of the user according to a first user distance detected by the first capacitive sensor, a second user distance detected by the second capacitive sensor, a first interval distance between the first capacitive sensor and the second capacitive sensor, and a second interval distance between the first pressure sensor or the second pressure sensor and the optical heart rate sensing module;

calculating and obtaining a relative offset angle between the optical heart rate sensing module and the wearing part of the user based on the first user distance, the second user distance, and the first interval distance.

6. The method according to claim 2, wherein the calculating and obtaining the relative position data of the optical heart rate sensing module and the wearing part of the user based on a plurality of user distances comprises:

calculating an average user distance from the plurality of the capacitive sensors to the wearing part of the user based on the plurality of the user distances;

determining the average user distance as a relative offset distance between the optical heart rate sensing module and the wearing part;

determining a third capacitive sensor and a fourth capacitive sensor with a largest user distance difference and central symmetric about the optical heart rate sensing module based on the plurality of the user distances; and calculating and obtaining the relative offset angle between the optical heart rate sensing module and the wearing part of the user based on a third user distance detected by the third capacitive sensor, a fourth user distance detected by the fourth capacitive sensor, and a third interval distance between the third capacitive sensor and the fourth capacitive sensor.

7. The method according to claim 5, wherein the calculating and obtaining the relative offset distance between the optical heart rate sensing module and the wearing part of the user according to the first user distance detected by the first capacitive sensor, the second user distance detected by the second capacitive sensor, the first interval distance between the first capacitive sensor and the second capacitive sensor, and the second interval distance between the first pressure sensor or the second pressure sensor and the optical heart rate sensing module comprises:

calculating and obtaining the relative offset distance between the optical heart rate sensing module and the wearing part of the user based on the first user distance, the second user distance, the first interval distance, and the second interval distance, in accordance with a calculation formula of the relative offset distance as below;

and wherein the calculation formula of the relative offset distance is: $h=(Ha-He)*Dcd/Dae$;

the calculating and obtaining the relative offset angle between the optical heart rate sensing module and the wearing part of the user based on the first user distance, the second user distance, and the first interval distance comprises:

calculating and obtaining the relative offset angle between the optical heart rate sensing module and the wearing part of the user based on the first user distance, the second user distance, and the first interval distance, in accordance with a calculation formula of the relative offset angle as below;

and wherein the calculation formula of the relative offset angle is: $\alpha=\arcsin[(Ha-He)/Dae]$;

Ha represents the first user distance, He represents the second user distance, Dae represents the first interval distance, and Dcd represents the second interval distance.

8. The method according to claim 1, wherein the calculating attenuation multiple of the reflection intensity based on the attenuation coefficient and the relative offset angle comprises:
calculating the attenuation multiple of the reflection intensity based on the attenuation coefficient and the relative offset angle, in accordance with a calculation formula of the attenuation multiple as below;
and wherein the calculation formula of the attenuation multiple is: $M=k(h)*\cos^2(\alpha)$;
M represents the attenuation multiple, h represents the relative offset distance, k(h) represents the attenuation coefficient corresponding to the relative offset distance h, and $\alpha$ represents the relative offset angle.

9. A wearable device, comprising a casing, a processor installed in the casing, and an optical heart rate sensing module and a distance sensing module connected to the processor and installed on a side of the casing facing a wearing part of a user; wherein
the optical heart rate sensing module is used for emitting an optical signal and detecting a reflection intensity of the optical signal; and sending the reflection intensity to the processor;
the distance sensing module is used for sending a positional relationship between the optical heart rate sensing module and a wearing part of the user to the processor; and
the processor is used for detecting the positional relationship between the optical heart rate sensing module and the wearing part of the user according to the distance sensing module, to obtain relative position data of the optical heart rate sensing module relative to the wearing part of the user; and adjusting a signal transmission power of the optical heart rate sensing module according to the relative position data, and detecting the heart rate of the user through the optical heart rate sensing module;
wherein the relative position data of the optical heart rate sensing module relative to the wearing part of the user comprises a relative offset distance and a relative offset angle;
the adjusting the signal transmission power of the optical heart rate sensing module according to the relative position data, and the detecting, by the optical heart rate sensing module, the heart rate of the user comprises:
determining an attenuation coefficient corresponding to the relative offset distance according to a preset attenuation parameter adjustment rule; wherein, the preset attenuation parameter adjustment rule is stored in the wearable device in advance, and the preset attenuation parameter adjustment rule comprises a corresponding relationship between the relative offset distance and the attenuation coefficient;
calculating attenuation multiple of a reflection intensity based on the attenuation coefficient and the relative offset angle; and
adjusting the signal transmission power of the optical heart rate sensing module in accordance with the attenuation multiple, and detecting, by the optical heart rate sensing module, the heart rate of the user.

10. The device according to claim 9, wherein the distance sensing module comprises a plurality of capacitive sensors; the optical heart rate sensing module is installed at a central position on the side of the casing facing the wearing part of the user, and the plurality of capacitive sensors surround a periphery of the optical heart rate sensing module at equal intervals by taking the optical heart rate sensing module as a center;
the processor is used for: for each capacitive sensor, calculating a user distance between a position point on the casing corresponding to the capacitive sensor and the wearing part of the user based on a capacitance parameter detected by the capacitive sensor; and calculating and obtaining the relative position data of the optical heart rate sensing module and the wearing part of the user based on a plurality of user distances.

11. The device according to claim 10, wherein the device further comprises a pressure sensing module connected to the processor and disposed on the side of the casing facing the wearing part of the user; the pressure sensing module comprises a plurality of pressure sensors; and the plurality of pressure sensors surround a periphery of the optical heart rate sensing module at equal intervals by taking the optical heart rate sensing module as a center, and are disposed at intervals with respect to the plurality of capacitive sensors;
the pressure sensing module is used for detecting and sending a pressure parameter between the casing and the wearing part of the user to the processor;
the processor calculating and obtaining the relative position data of the optical heart rate sensing module and the wearing part of the user based on the plurality of the user distances comprises:
determining a first pressure sensor and a second pressure sensor corresponding to a first largest and a second largest pressure parameters respectively based on each pressure parameter;
determining a capacitive sensor located between the first pressure sensor and the second pressure sensor as a first capacitive sensor and a second capacitive sensor central symmetric to the first capacitive sensor about the optical heart rate sensing module; and calculating and obtaining the relative position data of the optical heart rate sensing module relative to the wearing part of the user according to the user distances detected by the first capacitive sensor and the second capacitive sensor.

12. The device of claim 9, wherein the optical heart rate sensing module comprises plurality sets of light emitting diode lights for emitting the optical signal, and one or more photodetectors for detecting an optical intensity of the optical signal reflected by the wearing part of the user.

13. The device according to claim 12, wherein the optical heart rate sensing module comprises one photodetector and two sets of the light emitting diode lights;
the photodetector is located at a center of the optical heart rate sensing module, and the two sets of light emitting diode lights are symmetrically disposed on the left side and right side of the photodetector, so that the photodetector detects the optical intensity of the optical signal reflected by the wearing part of the user.

14. The device according to claim 9, further comprising a fixing belt connected to the casing; and the fixing belt is used for fixing the wearable device to the wearing part of the user.

15. The device according to claim 14, wherein the two ends of the casing are connected to the fixing belt; the distance sensing module comprises four capacitive sensors; the four capacitive sensors surround a periphery of the optical heart rate sensing module at equal intervals by taking the optical heart rate sensing module as a center; and wherein two capacitive sensors of the four capacitive sensors are disposed at the two ends of the casing connected to the fixing belt respectively.

16. The device according to claim 15, further comprising a pressure sensing module; wherein the pressure sensing module comprises four pressure sensors; the four pressure sensors and the four capacitance sensors are disposed at equal intervals, and surround a periphery of the optical heart rate sensing module at equal intervals.

* * * * *